US012778448B2

(12) United States Patent
Seo et al.

(10) Patent No.: US 12,778,448 B2
(45) Date of Patent: Nov. 3, 2026

(54) TECHNIQUES FOR MODEL-BASED LUNG FLUID STATUS DETECTION

(71) Applicant: Analog Devices, Inc., Wilmington, MA (US)

(72) Inventors: Joohyun Seo, Medford, MA (US); Tony J. Akl, Bedford, MA (US)

(73) Assignee: Analog Devices, Inc., Wilmington, MA (US)

( * ) Notice: Subject to any disclaimer, the term of this patent is extended or adjusted under 35 U.S.C. 154(b) by 604 days.

(21) Appl. No.: 18/265,815

(22) PCT Filed: Dec. 6, 2021

(86) PCT No.: PCT/US2021/061939
§ 371 (c)(1),
(2) Date: Jun. 7, 2023

(87) PCT Pub. No.: WO2022/125409
PCT Pub. Date: Jun. 16, 2022

(65) Prior Publication Data

US 2024/0115156 A1 Apr. 11, 2024

Related U.S. Application Data

(60) Provisional application No. 63/124,206, filed on Dec. 11, 2020.

(51) Int. Cl.
*A61B 5/085* (2006.01)
*A61B 5/00* (2006.01)
(Continued)

(52) U.S. Cl.
CPC ............ *A61B 5/086* (2025.01); *A61B 5/0537* (2013.01); *A61B 5/25* (2021.01); *A61B 5/6823* (2013.01);
(Continued)

(58) Field of Classification Search
CPC ......... A61B 5/086; A61B 5/25; A61B 5/0537; A61B 5/0536
See application file for complete search history.

(56) References Cited

U.S. PATENT DOCUMENTS 5,280,429 A * 1/1994 Withers .............. A61B 5/0537 378/70
6,435,182 B1 8/2002 Lutchen et al.
(Continued)

FOREIGN PATENT DOCUMENTS

EP 3052018 A1 8/2016
JP 2012-090880 A 5/2012
(Continued)

OTHER PUBLICATIONS

European Search Report and Search Opinion received for European Application No. 21904165, mailed on Mar. 27, 2024, 9 pages.
(Continued)

*Primary Examiner* — Daniel L Cerioni
(74) *Attorney, Agent, or Firm* — ArentFox Schiff LLP

(57) ABSTRACT

One embodiment is a method of performing thoracic tomography on a human subject including performing multiple 4-wire impedance measurements on a region of interest to obtain measured impedance data; comparing the measured impedance data to simulated impedance data obtained from a plurality of models of the region of interest; for each of the models, determining a fit of the model based on a comparison between the simulated impedance data obtained from the model and the measured impedance data; and integrating individual resistivity estimates obtained from the models based on a fit of the model such that the individual resistivity estimate from a better fitting model is weighted more heavily in a final resistivity estimate than an individual resistivity estimate from a worse fitting model.

44 Claims, 9 Drawing Sheets

(51) Int. Cl.
*A61B 5/0537* (2021.01)
*A61B 5/25* (2021.01)
*A61B 5/0536* (2021.01)

(52) U.S. Cl.
CPC .......... *A61B 5/6831* (2013.01); *A61B 5/0536* (2013.01); *A61B 2562/04* (2013.01)

(56) References Cited

U.S. PATENT DOCUMENTS

| | | | | |
|---|---|---|---|---|
| 2003/0212319 | A1* | 11/2003 | Magill | A61B 5/6804 600/382 |
| 2005/0124908 | A1 | 6/2005 | Belalcazar et al. | |
| 2006/0184060 | A1 | 8/2006 | Belalcazar et al. | |
| 2010/0113962 | A1* | 5/2010 | Hettrick | A61B 5/0538 600/547 |
| 2012/0056620 | A1* | 3/2012 | Feinberg | G01R 33/4835 324/309 |
| 2014/0046205 | A1* | 2/2014 | Arad (Abboud) | A61B 5/7289 600/513 |
| 2014/0276166 | A1 | 9/2014 | Drori et al. | |
| 2014/0358021 | A1 | 12/2014 | Cuba Gyllensten et al. | |
| 2015/0297099 | A1 | 10/2015 | Arad (Abboud) et al. | |
| 2016/0135741 | A1 | 5/2016 | Chetham et al. | |
| 2016/0143553 | A1* | 5/2016 | Chien | A61B 5/746 600/512 |
| 2016/0242673 | A1 | 8/2016 | Grychtol et al. | |
| 2020/0138335 | A1* | 5/2020 | Stender | A61B 5/0044 |
| 2021/0001119 | A1* | 1/2021 | Ordonez Orellana | A61B 5/6847 |
| 2021/0027461 | A1* | 1/2021 | Santos | G16H 30/40 |

FOREIGN PATENT DOCUMENTS

| | | | |
|---|---|---|---|
| JP | 2015-510427 | A | 4/2015 |
| JP | 2016-527943 | A | 9/2016 |
| WO | 2018104888 | A1 | 6/2018 |

OTHER PUBLICATIONS

International Search Report and Written Opinion issued in corresponding International Application No. PCT/US2021/061939 dated Feb. 24, 2022.

* cited by examiner

TECHNIQUES FOR MODEL-BASED LUNG FLUID STATUS DETECTION

RELATED APPLICATIONS

This application is a 35 U.S.C. § 371 National Stage Application of International Patent Application No. PCT/US2021/061939, filed Dec. 6, 2021, which application claims the benefit of and priority to U.S. Provisional Patent Application No. 63/124,206, filed Dec. 11, 2020, the contents of each of which applications are hereby incorporated herein by reference in their entireties.

FIELD OF THE DISCLOSURE

This disclosure relates generally to the field of lung fluid tomography and, more particularly, to techniques for model-based lung fluid status detection using multiple impedance measurements in combination with a priori knowledge of a region of interest.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Lung resistivity is a physiological parameter that describes the electrical characteristics of the lungs. Lung composition changes due to changes in the lung tissues, fluid and air volume. Various diseases that can cause a change in lung composition may be monitored by measuring lung resistivity. Lung fluid status is one such change in lung composition that may be monitored by measuring lung resistivity.

In certain embodiments, a thoracic impedance (Z) measurement system is an inexpensive non-invasive system for assessing lung resistivity, and therefore lung fluid status, and is available in a wearable form-factor for enabling home use and monitoring. In some embodiments, the thoracic impedance measurement may be accomplished using four electrodes.

Figure 1:
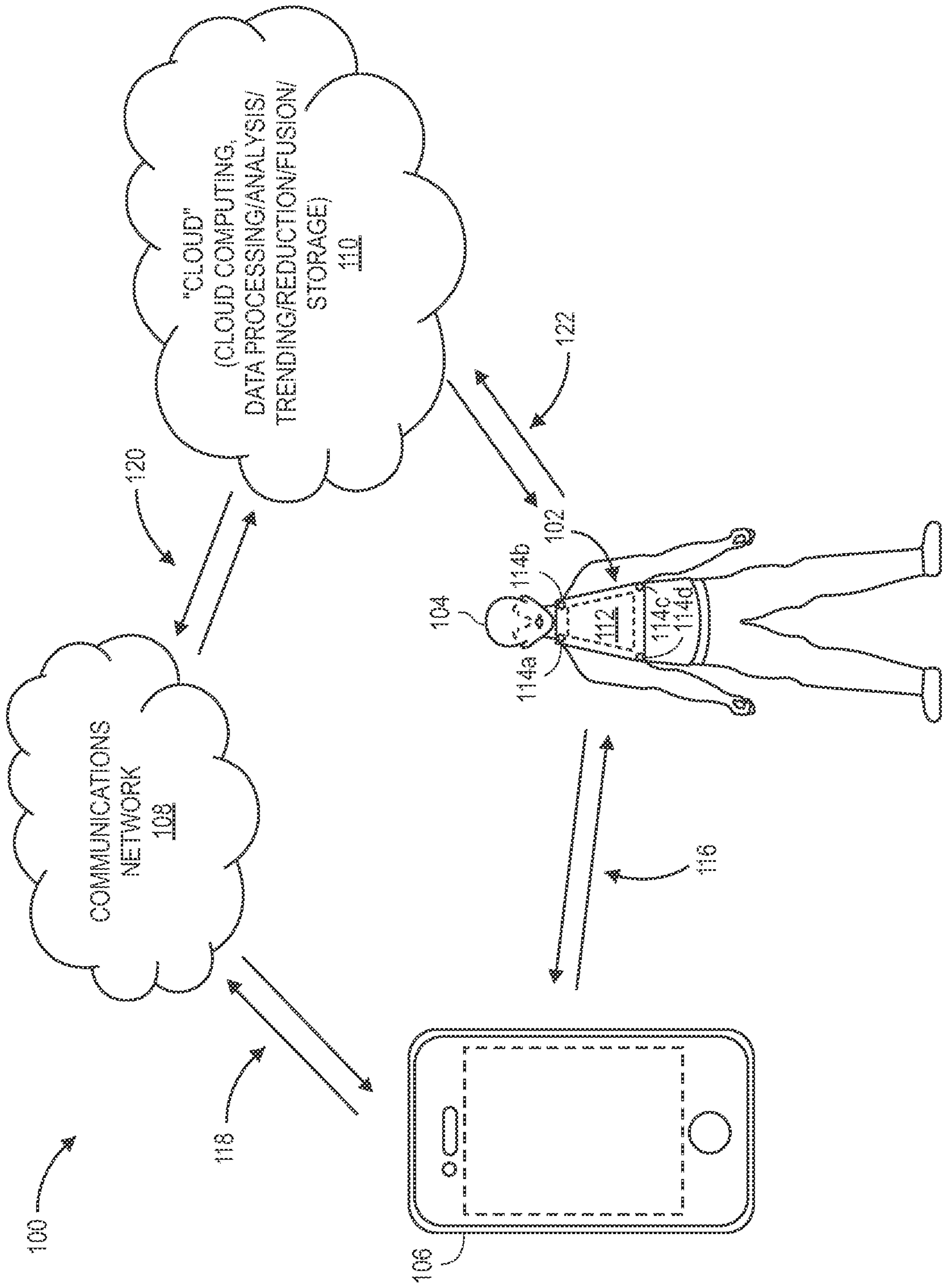
FIG. 1 illustrates an example environment in which an illustrative system for model-based lung fluid status detection according to some embodiments of the disclosure.

FIG. 1 depicts an example environment 100 in which an illustrative embodiment of a system 102 for performing model-based lung fluid status detection in human subjects according to some embodiments of the disclosure. The monitoring may be performed in a continuous or periodic fashion. As shown in FIG. 1, in accordance with one example embodiment, the system 102 includes a 4-wire thoracic impedance measurement module 112 and a plurality of surface electrodes/sensors 114*a*-114*d* (e.g., four (4) surface electrodes/sensors, or any other suitable number of surface electrodes/sensors). For example, one or more of the surface electrodes can be implemented as solid-gel surface electrodes, or any other suitable surface electrodes. The system 102 can be configured as a generally triangular-shaped device, or any other suitably shaped device, operative to make contact with one or more of the torso, upper chest, and neck areas, or any other suitable parts or areas of the body, of a human subject 104 via at least the plurality of surface electrodes/sensors 114*a*-114*d*.

In various implementations, the system 102 can have a configuration that allows it to be implemented within a wearable vest-like structure, as multiple patch-like devices, or any other suitable structure or device(s). In one possible environment, such as the environment 100, the system 102 may be operative to engage in bidirectional communications over wireless communication paths 116 with a smartphone 106, which, in turn, may be operative to engage in bidirectional communications over wireless communication paths 118 with a communications network 108 (e.g., the Internet). Alternatively, a direct link to the cloud 110 may be provided without requiring a hop through a base station or cell phone. The smartphone 106 is further operative, via the communications network 108, to engage in bidirectional communications over wireless communication paths 120 with the cloud 110, which can include resources for cloud computing, data processing, data analysis, data trending, data reduction, data fusion, data storage, and other functions. The system 102 is further operative to engage in bidirectional communications over wireless communication paths 122 directly with the cloud 110.

Figure 2:
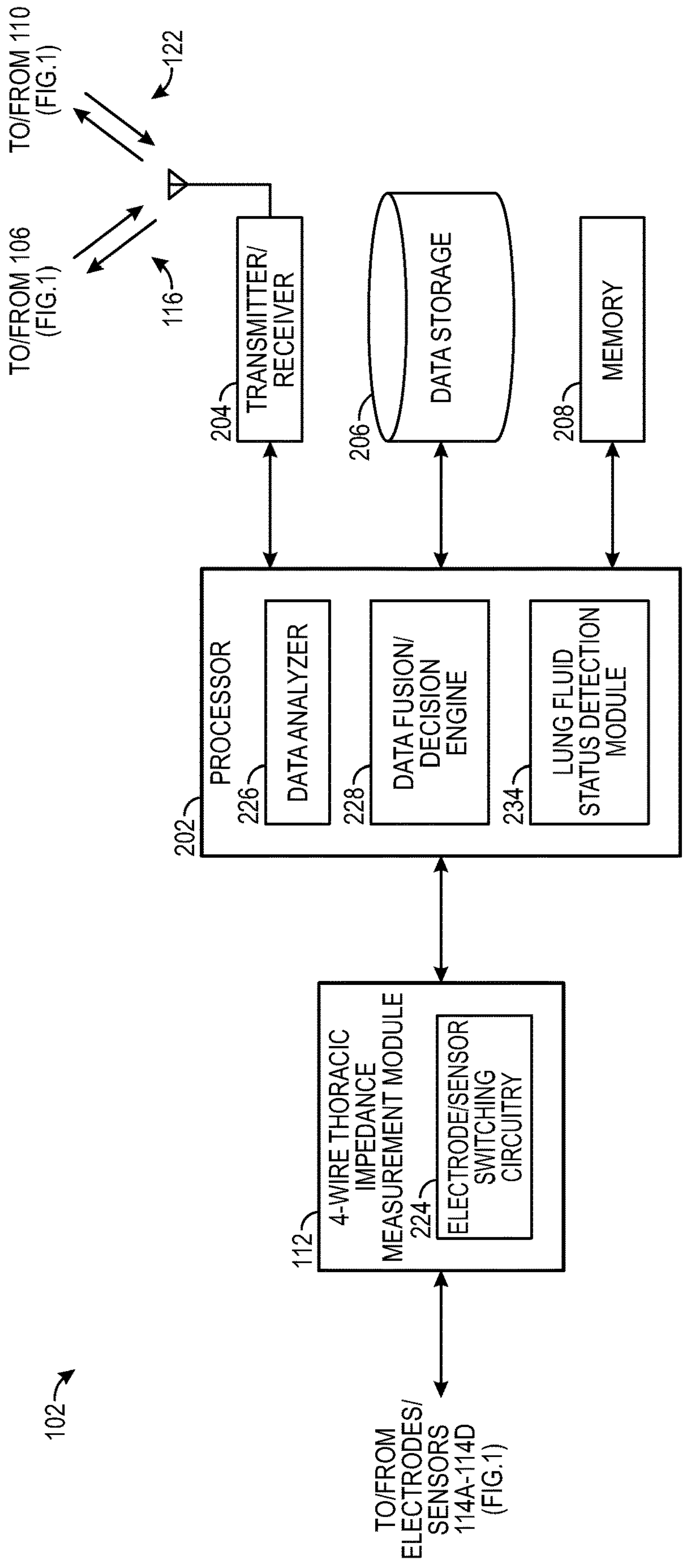
FIG. 2 is a block diagram illustrating exemplary functional components of the system of FIG. 1, according to some embodiments of the disclosure.

FIG. 2 depicts an example block diagram of the system 102 for performing model-based lung fluid status detection in human subjects according to some embodiments of the disclosure. As shown in FIG. 2, the system includes the thoracic impedance measurement module 112, a processor 202 and associated memory 208, a data storage 206 for storing thoracic impedance, lung resistivity, models, and related data, and a transmitter/receiver 204. The transmitter/receiver 204 can be configured to perform Bluetooth communications, Wi-Fi communications, or any other suitable short-range communications for communicating with the smartphone 106 (FIG. 1) over the wireless communication paths 116. The transmitter/receiver 204 can be further configured to perform cellular communications or any other suitable long-range communications for communicating with the cloud 110 (FIG. 1) over the wireless communication paths 122. In certain embodiments, the thoracic impedance measurement module 112 may further include electrode/sensor connection switching circuitry 224 for switchably making connections with the plurality of surface electrodes/sensors 114*a*-114*d* shown in FIG. 1.

The processor 202 can include a plurality of processing modules such as a data analyzer 226 and a data fusion/decision engine 228. The transmitter/receiver 204 can include at least one antenna 210 operative to transmit/receive wireless signals such as Bluetooth or Wi-Fi signals over the wireless communications paths 116 to/from the smartphone 106, which can be a Bluetooth or Wi-Fi-enabled smartphone or any other suitable smartphone. The antenna 210 is further operative to transmit/receive wireless signals such as cellular signals over the wireless communications paths 122 to/from the cloud 110.

The processor 202 can further include a lung fluid status detection module 234 for performing model-based lung fluid status detection in human subjects in accordance with embodiments described herein and as described in greater detail below. It will be recognized that all or a portion of the processor 202, as well as modules shown as forming a part of the processor 202 (e.g., a portion or all of lung fluid status detection module 234), may additionally and/or alternatively be implemented in the cloud 110 (FIG. 1) and may actually comprise multiple processors and/or processing elements for implementing the techniques described herein. It will be further recognized that other elements shown in FIG. 2 as comprising part of the system 102 may be additionally and/or alternatively reside in the cloud 110 (FIG. 1). In certain embodiments, the processor 202 may comprise a controller for controlling operations of measurement module/circuitry.

The transmitter/receiver 204 can include at least one antenna 210 operative to transmit/receive wireless signals such as Bluetooth or Wi-Fi signals over the wireless communications paths 116 to/from the smartphone 106, which can be a Bluetooth or Wi-Fi-enabled smartphone or any other suitable smartphone. The antenna 210 is further operative to transmit/receive wireless signals such as cellular signals over the wireless communications paths 122 to/from the cloud 110.

The operation of the system 102 for performing model-based lung fluid status detection in human subjects according to some embodiments will be further understood with reference to the following illustrative example, as well as FIGS. 1 and 2. In this illustrative example, at fixed times each day (e.g., two times per day) or continuously for a predetermined number of days while the human subject 104 is in a supine or upright position, the human subject or a human assistant positions the system 102 configured as the generally triangular-shaped device (or any other suitably shaped device) such that it makes contact with one or more of the subject's torso and upper chest and neck areas (or any other suitable parts or areas of the body) via the plurality of surface electrodes/sensors 114*a*-114*d*.

Having positioned the system 102 in contact with the human subject's torso and/or upper chest and/or neck areas, the 4-wire thoracic impedance measurement module 112 can be activated to gather, collect, sense, measure, or otherwise obtain thoracic impedance data from the human subject 104 and generate signals indicative thereof.

The 4-wire thoracic impedance measurement module 112 can perform thoracic impedance measurements using some or all of the plurality of surface electrodes 114*a*-114*d* that make contact with the skin of the human subject 104 on his or her torso, upper chest, and/or neck areas In some embodiments, the thoracic impedance data from the thoracic impedance measurement module 112 may be provided to the data analyzer 226 for at least partial data analysis, data trending, and/or data reduction. In one embodiment, the thoracic impedance measurement data in combination with other metadata, such as medical history, demographic information, and other testing modalities, can also be analyzed, trended, and/or reduced "in the cloud" and made available in cloud-based data storage 110 with pre-set alerts for use in various levels of clinical interventions with respect to respiratory parameters.

The data analyzer 226 may provide the at least partially analyzed thoracic impedance data to the data fusion/decision engine 228, which may effectively at least partially fuse or combine the thoracic impedance data with other sensing data, in accordance with one or more algorithms and/or decision criteria, for subsequent use in making one or more inferences about the human subject 104. The processor 202 may then provide the at least partially combined thoracic impedance and other sensing data to the transmitter/receiver 204, which may transmit the combined thoracic impedance and sensing data either directly over the wireless communication paths 122 to the cloud 110, or over the wireless communication paths 116 to the smartphone 106. Next, the smartphone 106 can transmit, via the communications network 108, the combined thoracic impedance and sensing data over the wireless communication paths 118, 120 to the cloud 110, where it can be further analyzed, trended, reduced, and/or fused. It will be recognized that, as described above, communications data may be communicated directly to the cloud 110 without involvement of a smartphone/cell phone or base station.

The resulting curated combined sensing data can then be remotely downloaded by hospital clinicians for risk scoring/stratification, monitoring and/or tracking purposes.

Figure 3:
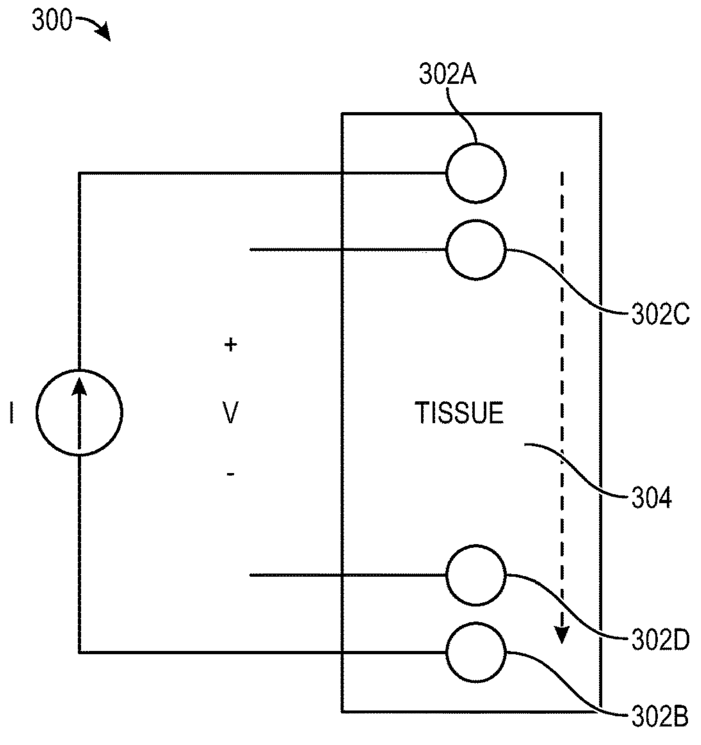
FIG. 3 illustrates operation of a 4-wire impedance measurement system in accordance with one embodiment.

FIG. 3 illustrates operation of a 4-wire thoracic impedance measurement system 300 in accordance with one embodiment. As shown in FIG. 3, the system includes four electrodes 302A-302D. In operation, an alternating electrical current at a fixed excitation frequency I is injected from one of four electrodes (e.g., electrode 302A) to another one of the four electrodes (e.g., electrode 302B) through a region of interest 304 (e.g., a lung) and a voltage difference V across the remaining two electrodes (e.g., electrodes 302C and 302D) is measured. An impedance (Z) may be determined from those values (i.e., Z=V/I). A change in impedance indicates a change in the region of interest 304.

As will be described in greater detail, in accordance with features of embodiments described herein, the technique may also be performed using measurements at multiple excitation frequencies, with the final clinically useful information being derived from a combination of the multiple excitation frequency results, as opposed to the just the result from a single excitation frequency.

4-wire thoracic impedance measurement systems, such as the system 300, suffer from certain limitations. For example, when the region of interest 304 has high resistivity, such as is the case with a lung, the calculated impedance Z is not sensitive and specific to the resistivity change. Additionally, a small change in lung fluid status is easily obscured by other factors.

Figure 4:
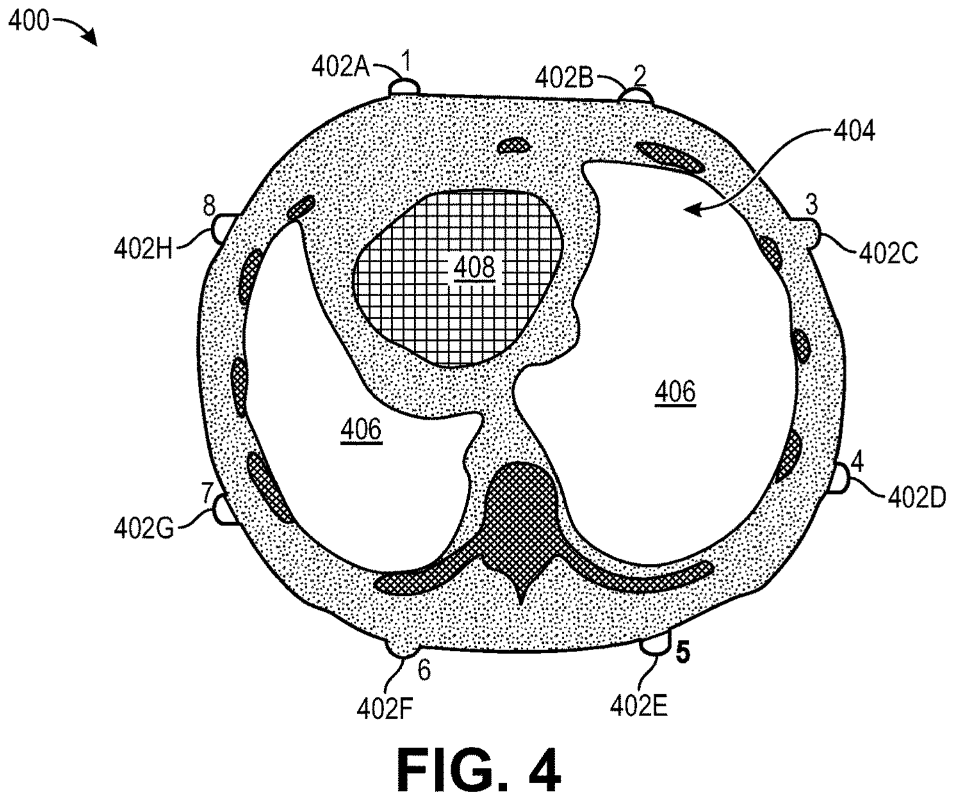
FIG. 4 illustrates an example electrical impedance tomography technique for lung fluid status detection in which multiple 4-wire impedance measurements using multiple (e.g., 8 or more) electrodes dispersed around a region of interest are performed to obtain a map of resistivity estimate without using any a priori knowledge of the region of interest.

Referring now to FIG. 4, illustrated therein is an electrical impedance tomography technique 400 for lung fluid status detection in which multiple 4-wire impedance measurements using multiple (e.g., 8 or more) electrodes 402A-

402H dispersed around a region of interest 404 are performed to obtain a map of resistivity estimate without using any a priori knowledge of the region of interest. As shown in FIG. 4, the region of interest 404 represents a human upper torso (or chest), including the individual's lungs 406 and heart 408.

In accordance with features of embodiments described herein, a model-based fluid status detection technique is performed using a limited number of (e.g., 5-6) electrodes in combination with a priori knowledge of the region of interest, or domain, with multiple 4-wire impedance measurements being performed to extract the domain information including the resistivity of the lung region ($\rho_{lung}$). Techniques described herein are more sensitive and specific to lung-fluid changes than a single 4-wire impedance measurement technique, while being less computationally heavy and complicated than traditional electrical impedance tomography techniques.

Figure 5:
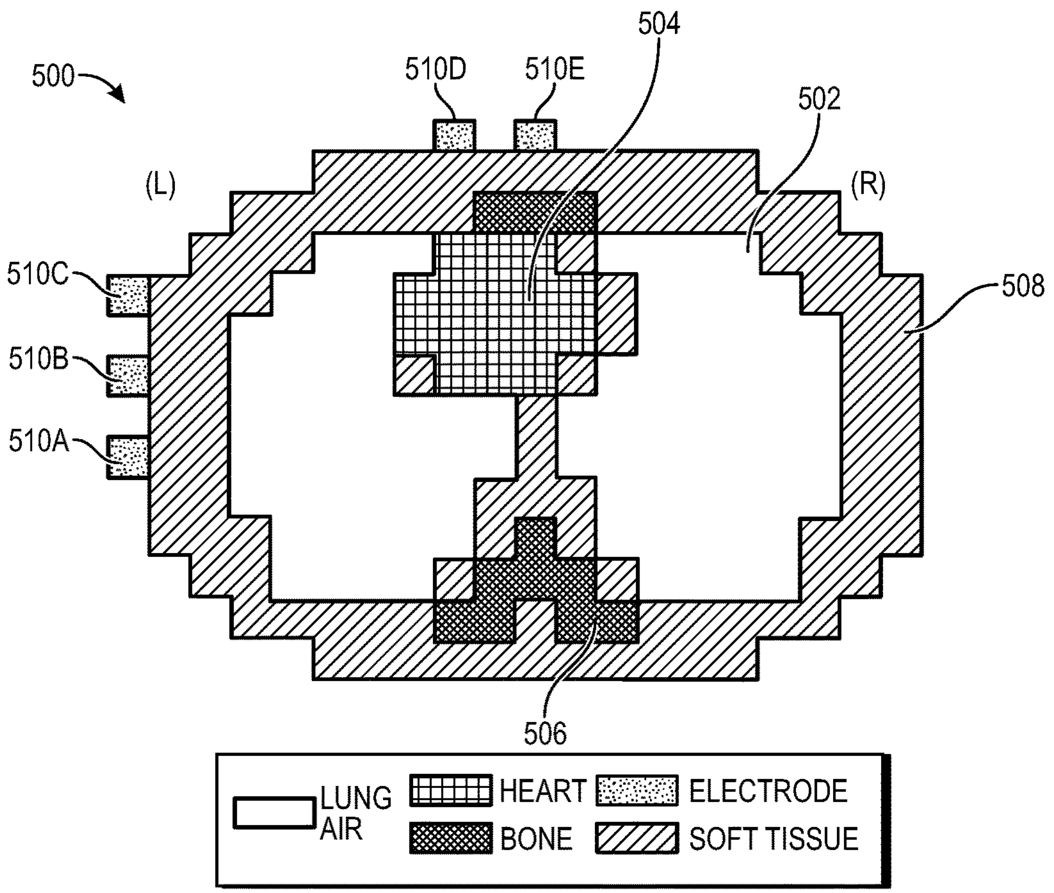
FIG. 5 illustrates a cross-sectional model of a human upper torso, showing various types of tissue (lung, heart, bone, and soft tissue) and air.

FIG. 5 illustrates a cross-sectional model 500 of a human upper torso (or chest), showing various types of tissue, including lungs 502, heart 504, bone 506, and soft tissue 508. Lungs 502 are filled with air. Example placement of the electrodes 510A-510E is also shown in FIG. 5. Lung resistivity (or lung fluid status) may be estimated within a single model, such as the model 500 shown in FIG. 5.

Figure 6:
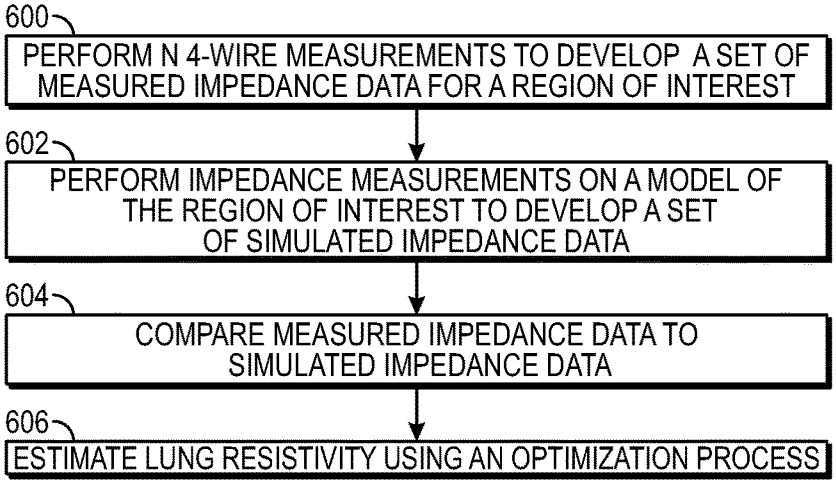
FIG. 6 is a flowchart illustrating operation of a model-based fluid status detection technique using a single model of a region of interest.

FIG. 6 is a flowchart illustrating operation of a model-based fluid status detection technique using a single model. In step 600, a number of (e.g., 5-6 (preferably fewer than 8)) electrodes are used to perform N 4-wire measurements to develop a set of measured impedance data $Z_{meas}=Z_1, Z_2, \ldots Z_N$ for a domain, or region, of interest. In step 602, simulated measurements are taken using a model of the domain of interest, such as the model 500 shown in FIG. 5. Model parameters (x), typically consisting of continuous variables including $\rho_{lung}$, determine simulated impedance measurements $Z_{sim}(x)=[Z_{sim1}, Z_{sim2}, Z_{simN}]$. In step 604, a selected portion or all of the measured impedance data is compared to a selected portion or all of the simulated impedance data. In step 606, lung resistivity estimation is performed through an optimization process, in which a set of x, including, $\rho_{lung}$, is identified that minimizes the cost function, for example, as described by but not limited to the following:

$$\min_x \|Z_{meas} - Z_{sim}(x)\|^2$$

Solving one inverse problem for estimating lung resistivity, such as described above, presents a variety of challenges. For example, the measurement condition is highly likely to be non-negligibly different from what is assumed (e.g., electrode placement, lung size, tissue placement) in the simulation model. As a result, the final result may be overly sensitive to factors other than lung fluid status.

Figure 7A:
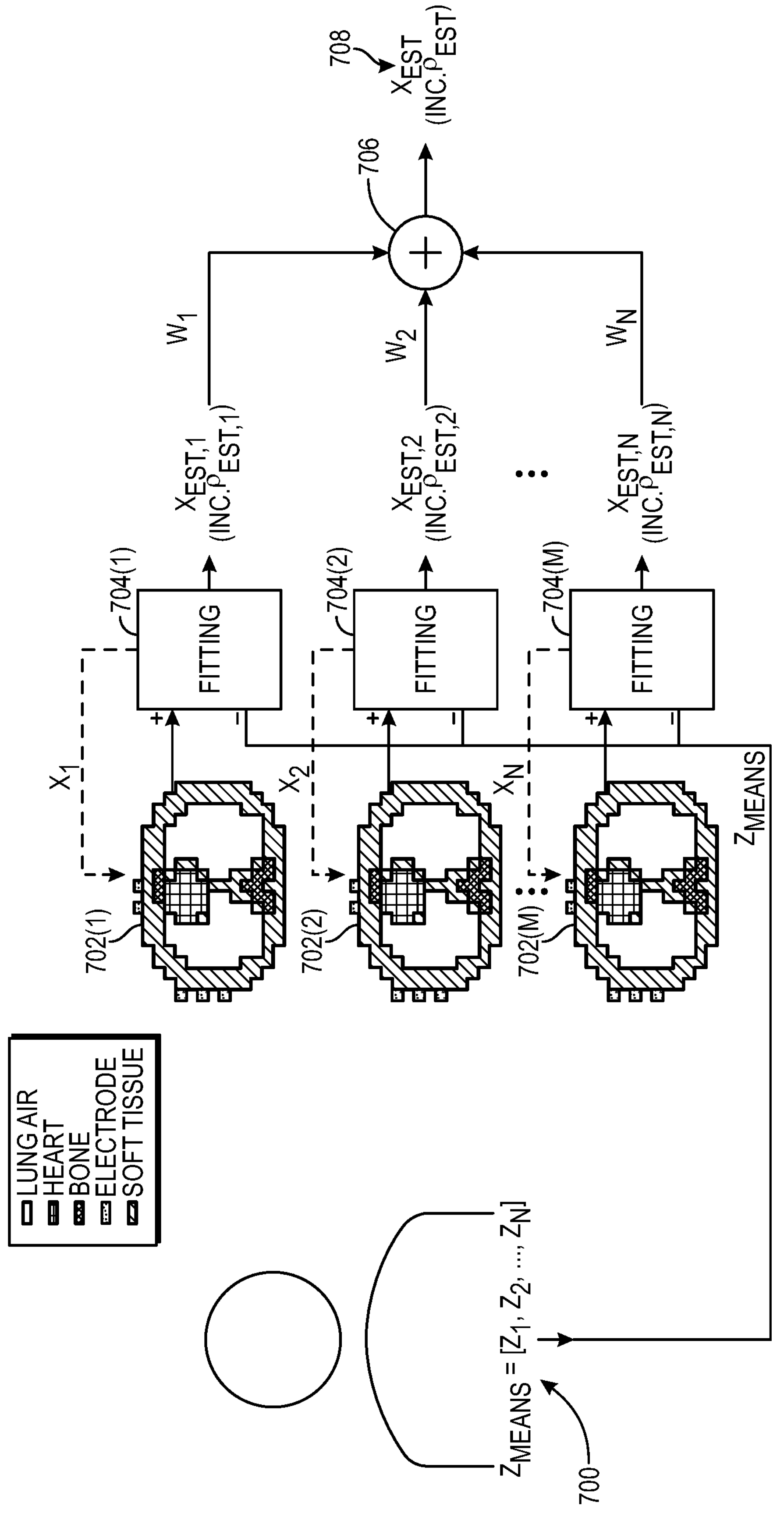
FIGS. 7A and 7B illustrates an example embodiment described herein for implementing a model-based lung fluid status detection system using multiple impedance measurements in combination with a priori knowledge of a region of interest.

In accordance with features of embodiments described herein, and in order to ensure that the final result is sensitive and specific to lung fluid change and not to other factors, a multiple inverse problem is solved and the results are summarized based on the "fit" between the measured data and each problem. Referring now to FIG. 7A, in one implementation, measured impedance data $Z_{meas}$ 700 of a region of interest (e.g., a human chest or upper torso) at a frequency f is compared to simulated impedance data Z sim obtained from each of M sample models 702(1)-702(M). Each of the M sample models 702(1)-702(M) represents a different possible combination of electrode placement and specific anatomical features (e.g., relative size and location of lung tissue, heart tissue, soft tissue, and bone) of the region of interest. A "fit" may be determined for each of the M models based on a comparison 704(1)-704(M) of the measured impedance data with the simulated impedance data from the model. Estimated model parameters for each of the models ($X_{est,1}$-$X_{est,N}$), which include individual resistivity estimates ($\rho_{est,1}$-$\rho_{est,N}$) for the models are integrated, or summarized 706, based on the "fit" between the measured data and the respective model to develop final model parameters ($X_{est}$), including a final resistivity estimate ($\rho_{est}$), 708 such that estimates from better "fitting" models are weighted more heavily in the final estimate than those from worse "fitting" models. For example, the final resistivity estimate may be a weighted mean of the individual estimates, with the weight ($W_1$-$W_N$) assigned to a model i, for example, defined by but not limited to:

$$1/f_{residual,cost,i}$$

where $f_{residual,cost}$ is the residual cost function value of the optimization for solving inverse problems. In the embodiment illustrated in FIG. 7A, one measurement is understood as numerous possible placements and anatomical geometry with its own likelihood, or weight.

It will be noted that thoracic impedance measurements may vary depending on the excitation frequencies used to make the measurements, due to underlying changes how the electric current flows in the region of interest. For example, at a first excitation frequency, measurements may be more sensitive to changes in soft tissue, whereas at a different excitation frequency, measurements may be more sensitive to changes in lung tissue.

Figure 7B:
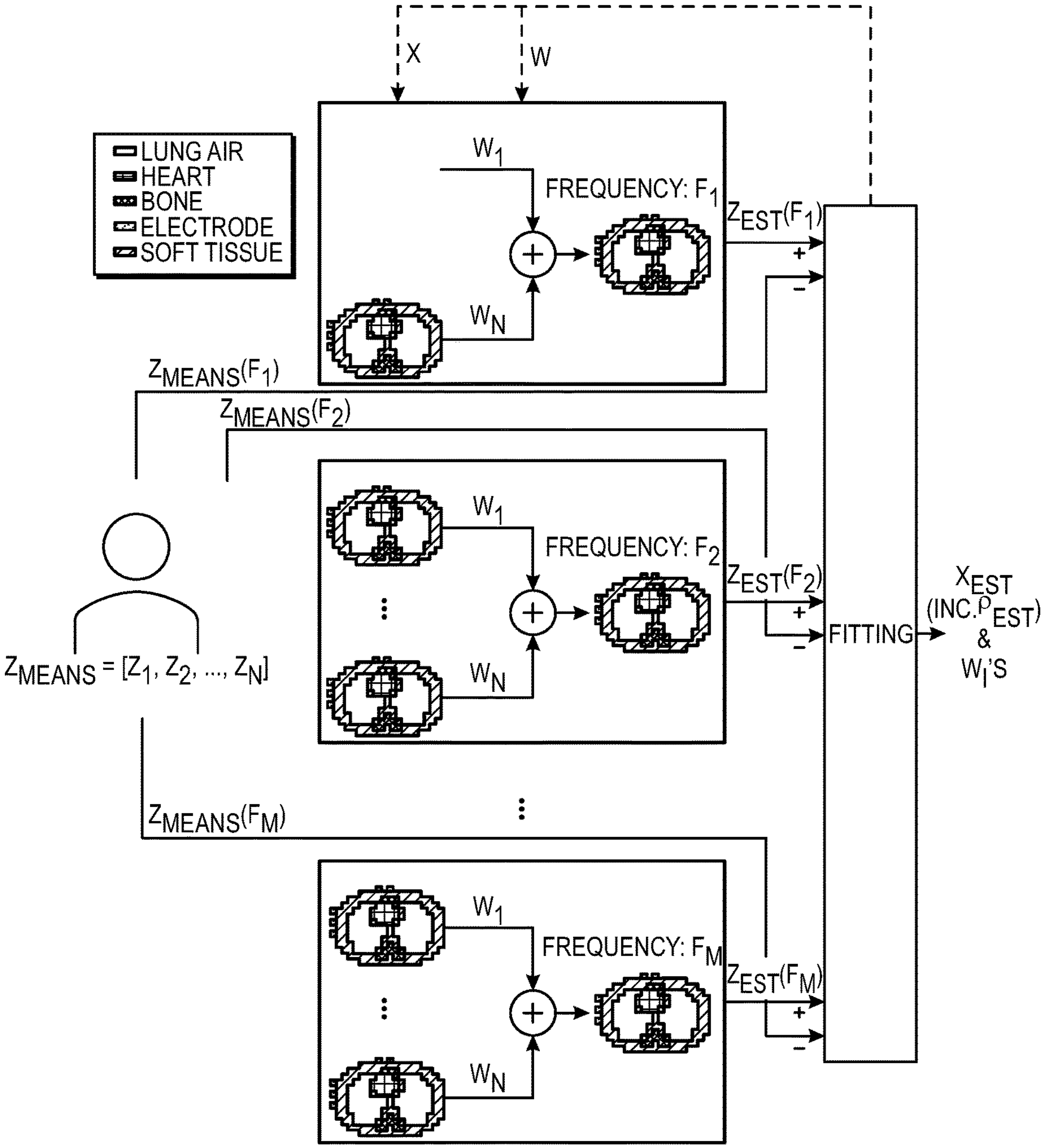

In accordance with aspects of embodiments described herein, as illustrated in FIG. 7B, the techniques illustrated in FIG. 7A may be applied to impedance data measured and estimated at each of multiple frequencies $f_1$-$f_m$ to generate measured impedance data $Z_{meas}(f_1)$-$Z_{meas}(f_m)$ and estimated (or simulated) impedance data $Z_{est}$ $(f_1)$-$Z_{est}(f_m)$. The results are combined by fitting $Z_{mass}(f_1)$-$Z_{meas}(f_m)$ to respective simulated impedance measurements $Z_{est}(f_1)$-$Z_{est}(f_m)$, thereby combining the data to develop final model parameters (Xest), including a final resistivity estimate (pest) such that estimates from better "fitting" models are weighted more heavily in the final estimate than those from worse "fitting" models across the range of frequencies. The resulting parameters used to generate final clinical insights regarding changes in the region of interest.

Figure 8A:
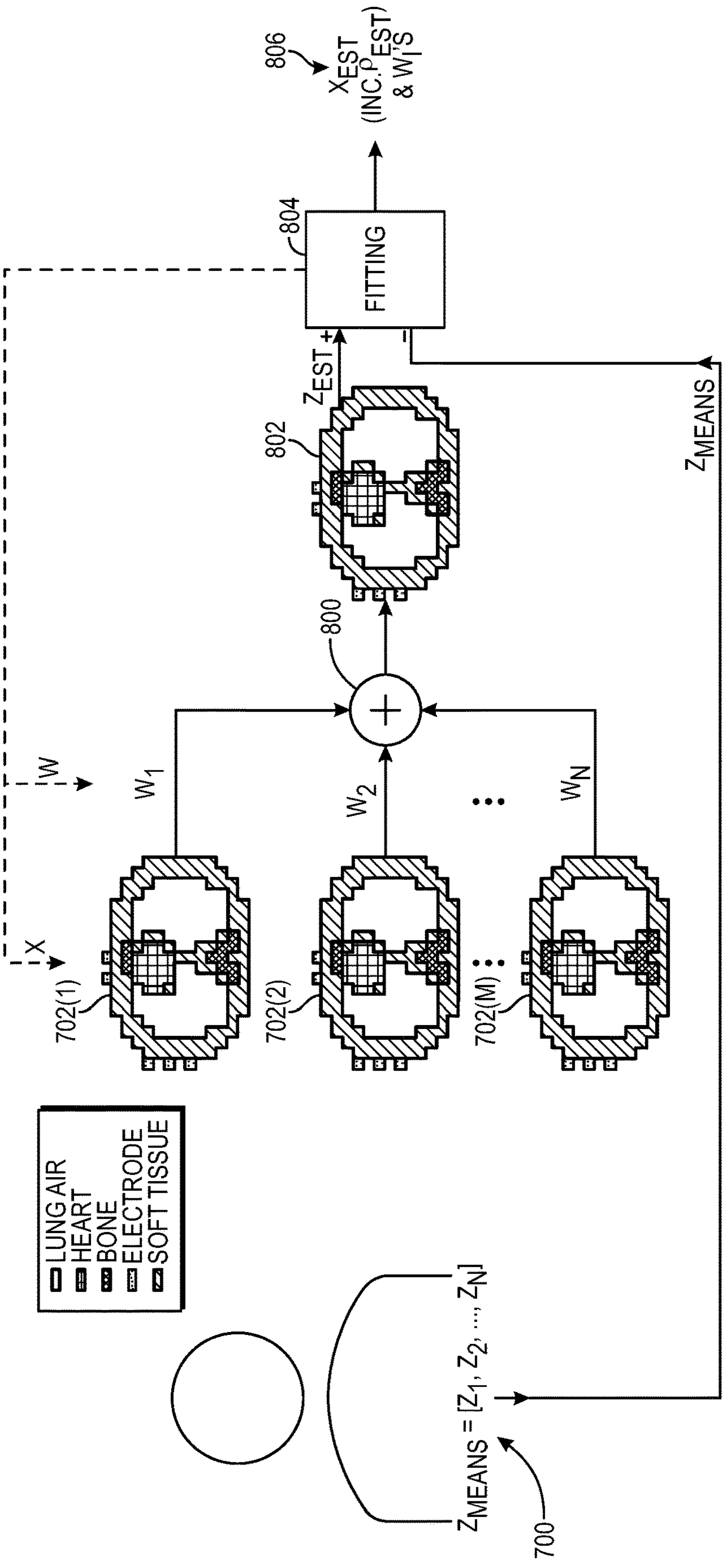
FIGS. 8A and 8B illustrates another example embodiment described herein for implementing a model-based lung fluid status detection system using multiple impedance measurements in combination with a priori knowledge of a region of interest.

FIG. 8A illustrates an alternative implementation in which the M models 702(1)-702(M) are "summarized" (via a mean of a weighted sum of the models) 800 into a single sample model 802 that is deemed to best represent the real measurement condition 700. The resulting single sample model 802 is used to produce estimated impedance data ($Z_{est}$) which is "fit" 804 to impedance data $Z_{meas}$ for producing final model parameters $X_{est}$, including a final resistivity estimate $\rho_{est}$, as well as the weights $W_1$ used in the weighted summation of the M sample models to produce the single sample model, 806.

Figure 8B:
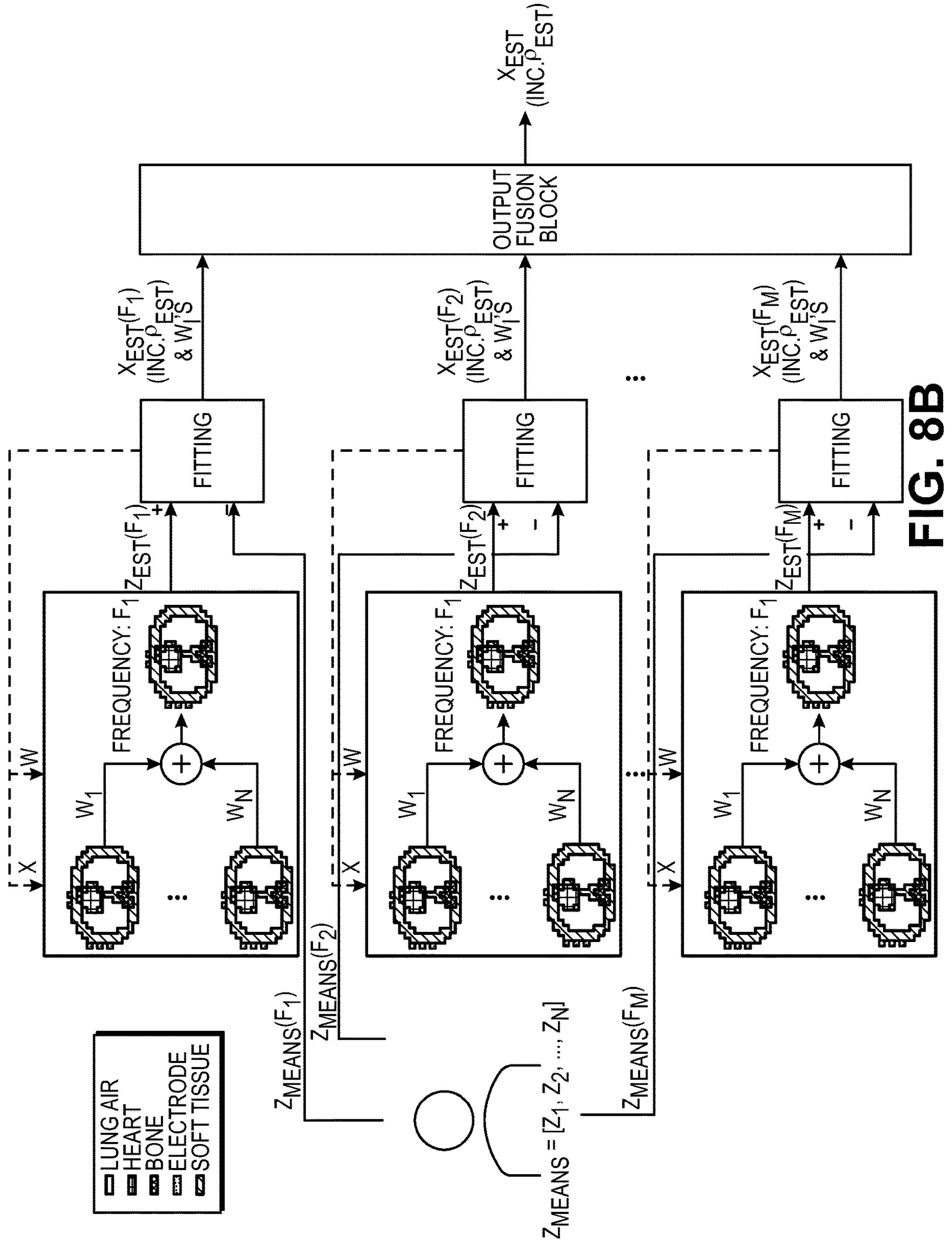

In accordance with aspects of embodiments described herein, as illustrated in FIG. 8B, the techniques illustrated in FIG. 8A may be executed for multiple excitation frequencies $f_1$-$f_m$ to generate model parameters $X_{est}$ $(f_1)$-$X_{est}(f_m)$, including final resistivity estimates $\rho_{estf1}$-$\rho_{estfm}$ as well as the weights $W_{if1}$-$W_{ifm}$. The resulting parameters are combined and used to generate final clinical insights regarding changes in the region of interest.

Figure 9:
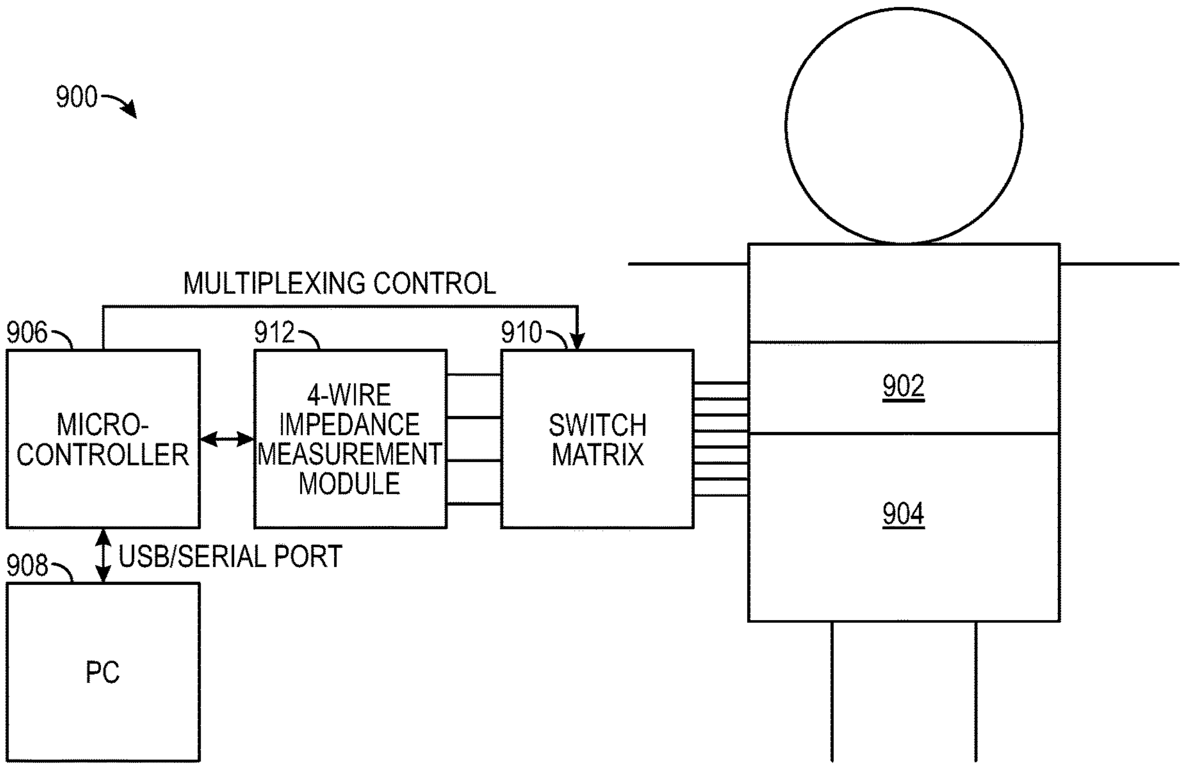
FIG. 9 illustrates a schematic block diagram of a system for performing thoracic impedance measurements on a human subject.

FIG. 9 illustrates a block diagram of an example system 900 for obtaining measured impedance data $Z_{meas}$ of a region of interest (e.g., lung) of a patient as described above. As shown in FIG. 9, an elastic chest band 902 having electrodes connected thereto is attached to the chest of a human subject 904. In the illustrated embodiment, three of the electrodes may be placed near the center of the chest of the subject 904 and three may be placed on the left side of the subject. A microcontroller unit (MCU) 906 under the control of a computer (PC) 908 controls the measurement sequence. In particular, the MCU 906 changes switch configuration 910 to perform different 4-wire impedance measurements using a 4-wire impedance measurement module 912 using the six (in the illustrated embodiment) electrodes placed on the chest of the subject 904.

It will be recognized that some or all of the processes, modules and/or devices illustrated in and described with reference to FIG. 9 may be implemented using some or all of the processes, modules and/or devices shown in and described with reference to FIG. 1 and/or FIG. 2 and vice versa.

Example 1 provides a method of detecting lung fluid status of a human subject, the method comprising performing multiple impedance measurements on a region of interest to obtain measured impedance data; comparing the measured impedance data to simulated impedance data obtained from a plurality of models of the region of interest; for each of the models, determining a fit of the model based on a comparison between the simulated impedance data obtained from the model and the measured impedance data; and integrating individual resistivity estimates obtained from the models based on a fit of the model such that the individual resistivity estimate from a better fitting model is weighted more heavily in a final resistivity estimate than an individual resistivity estimate from a worse fitting model.

Example 2 provides the method of example 1, wherein the performing multiple impedance measurements comprises performing multiple 4-wire impedance measurements.

Example 3 provides the method of example 2, wherein a maximum of eight electrodes are used to perform the multiple 4-wire impedance measurements.

Example 4 provides the method of any of examples 1-3, wherein each of the models represents a different possible combination of electrode placement and a specific anatomical feature of the human subject.

Example 5 provides the method of example 4, wherein the specific anatomical features comprise at least one of a relative size and location of lung tissue, heart tissue, soft tissue, and bone.

Example 6 provides the method of any of examples 1-3, wherein the final resistivity estimate is a weighted mean of the individual resistivity estimates.

Example 7 provides the method of example 6, wherein a weight assigned to a model N is defined by $1/f_{residual,cost,N}$, where $f_{residual,cost}$ is a residual cost function value of an optimization for solving inverse problems.

Example 8 provides the method of any of examples 1-3, further comprising developing a single sample model using a weighted sum of the plurality of models based on a respective fit of the models.

Example 9 provides the method of any of examples 1-3, wherein the multiple impedance measurements are performed at a single excitation frequency.

Example 10 provides the method of any of examples 1-3, wherein the multiple impedance measurements are performed at multiple excitation frequencies.

Example 11 provides the method of example 10, further comprising executing the comparing, the determining, and the integrating for each of the excitation frequencies.

Example 12 provides a system for detecting lung fluid status of a human subject, the system comprising a plurality of electrodes on a chest of the human subject; a thoracic impedance detection module connected to the electrodes, the thoracic impedance detection module configured to perform multiple impedance measurements on a region of interest to obtain measured impedance data; compare the measured impedance data to simulated impedance data obtained from a plurality of models of the region of interest; for each of the models, determine a fit of the model based on a comparison between the simulated impedance data obtained from the model and the measured impedance data; and integrate individual resistivity estimates obtained from the models based on a fit of the model such that the individual resistivity estimate from a better fitting model is weighted more heavily in a final resistivity estimate than an individual resistivity estimate from a worse fitting model.

Example 13 provides the system of example 12, wherein the performing multiple impedance measurements comprises performing multiple 4-wire impedance measurements.

Example 14 provides the system of any of examples 12-13, wherein the electrodes are connected to an elastic chest strap for attaching around a chest of the human subject to ensure correct location of the electrodes relative to the region of interest.

Example 15 provides the system of any of examples 12-13, wherein each of the models represents a different possible combination of electrode placement and a specific anatomical feature of the human subject.

Example 16 provides the system of example 15, wherein the specific anatomical features comprise at least one of a relative size and location of lung tissue, heart tissue, soft tissue, and bone.

Example 17 provides the system of any of examples 12-13, wherein the final resistivity estimate is a weighted mean of the individual resistivity estimates.

Example 18 provides the system of example 17, wherein a weight assigned to a model N is defined by $1/f_{residual,cost,N}$, where $f_{residual,cost}$ is a residual cost function value of an optimization for solving inverse problems.

Example 19 provides the system of any of examples 12-13, wherein the thoracic impedance detection module is further configured to develop a single sample model using a weighted sum of the plurality of models based on a respective fit of the models.

Example 20 provides the system of any of examples 12-13, wherein the plurality of electrodes comprises fewer than eight electrodes.

Example 21 provides the system of any of examples 12-13, wherein the plurality of electrodes further comprises three electrodes on the front of the chest and three of the electrodes on the left side of the chest.

Example 22 provides the system of any of examples 12-13, wherein the multiple impedance measurements are performed at a single excitation frequency.

Example 23 provides the system of any of examples 12-13, wherein the multiple impedance measurements are performed at multiple excitation frequencies.

Example 24 provides the system of example 23, wherein the thoracic impedance detection module is further configured to execute the comparing, the determining, and the integrating for each of the excitation frequencies.

Example 25 provides a method of detecting lung fluid status of a human subject, the method comprising performing multiple impedance measurements on a region of interest to obtain measured impedance data; summarizing a plurality of models of the region of interest into a single sample model that represents the region of interest; generating simulated impedance data using the single sample model; fitting the simulated impedance data to the measured impedance data to produce a final resistivity estimate for the region of interest.

Example 26 provides the method of example 25, further comprising, prior to the summarizing, applying a weight to each of the models to produce weighted models.

Example 27 provides the method of example 26, wherein the summarizing further comprises computing a mean of a sum of weighted models.

Example 28 provides the method of example 26, further comprising fitting the simulated impedance data to the measured impedance data to produce weights applied to the models.

Example 29 provides the method of any of examples 25-28, wherein the performing multiple impedance measurements comprises performing multiple 4-wire impedance measurements.

Example 30 provides the method of example 29, wherein fewer than eight electrodes are used to perform the multiple 4-wire impedance measurements.

Example 31 provides the method of any of examples 25-28, wherein each of the models represents a different possible combination of electrode placement and a specific anatomical feature of the human subject.

Example 32 provides the method of example 31, wherein the specific anatomical features comprise at least one of a relative size and location of lung tissue, heart tissue, soft tissue, and bone.

Example 33 provides the method of any of examples 25-28, wherein the multiple impedance measurements are performed at a single excitation frequency.

Example 34 provides the method of any of examples 25-28, wherein the multiple impedance measurements are performed at multiple excitation frequencies.

Example 35 provides the method of example 34, further comprising executing the summarizing, the generating, and the fitting for each of the excitation frequencies.

Example 36 provides a system for detecting lung fluid status of a human subject, the system comprising a plurality of electrodes on a chest of the human subject; a thoracic impedance detection module connected to the electrodes, the thoracic impedance detection module for performing multiple impedance measurements on a region of interest to obtain measured impedance data; summarizing a plurality of models of the region of interest into a single sample model that represents the region of interest; generating simulated impedance data using the single sample model; and fitting the simulated impedance data to the measured impedance data to produce a final resistivity estimate for the region of interest.

Example 37 provides the system of example 36, wherein the performing multiple impedance measurements comprises performing multiple 4-wire impedance measurements.

Example 38 provides the system of any of examples 36-37, wherein the electrodes are connected to an elastic chest strap for attaching around a chest of the human subject to ensure correct location of the electrodes relative to the region of interest.

Example 39 provides the system of any of examples 36-37, wherein each of the models represents a different possible combination of electrode placement and a specific anatomical feature of the human subject.

Example 40 provides the system of example 39, wherein the specific anatomical features comprise at least one of a relative size and location of lung tissue, heart tissue, soft tissue, and bone.

Example 41 provides the system of any of examples 36-37, wherein the thoracic impedance detection module is further configured to develop a single sample model using a weighted sum of the plurality of models based on a respective fit of the models.

Example 42 provides the system of any of examples 36-37, wherein the plurality of electrodes comprises fewer than eight electrodes.

Example 43 provides the system of any of examples 36-37, wherein the plurality of electrodes further comprises three electrodes on the front of the chest and three of the electrodes on the left side of the chest.

Example 44 provides the system of any of examples 36-37, wherein the multiple impedance measurements are performed at a single excitation frequency.

Example 45 provides the system of any of examples 36-37, wherein the multiple impedance measurements are performed at multiple excitation frequencies.

Example 46 provides the system of example 45, further comprising the thoracic impedance detection module performing the summarizing, the generating, and the fitting for each of the excitation frequencies.

It should be noted that all of the specifications, dimensions, and relationships outlined herein (e.g., the number of elements, operations, steps, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, exemplary embodiments have been described with reference to particular component arrangements. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system may be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and may accommodate a large number of components, as well as more complicated/sophisticated arrangements and configurations. Accordingly, the examples provided should not limit the scope or inhibit the broad teachings of the electrical circuits as potentially applied to myriad other architectures.

It should also be noted that in this Specification, references to various features (e.g., elements, structures, modules, components, steps, operations, characteristics, etc.) included in "one embodiment", "exemplary embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It should also be noted that the functions related to circuit architectures illustrate only some of the possible circuit architecture functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Note that all optional features of the device and system described above may also be implemented with respect to the method or process described herein and specifics in the examples may be used anywhere in one or more embodiments.

The "means for" in these instances (above) may include (but is not limited to) using any suitable component discussed herein, along with any suitable software, circuitry, hub, computer code, logic, algorithms, hardware, controller, interface, link, bus, communication pathway, etc.

Note that with the example provided above, as well as numerous other examples provided herein, interaction may be described in terms of two, three, or four network elements. However, this has been done for purposes of clarity and example only. In certain cases, it may be easier to describe one or more of the functionalities of a given set of flows by only referencing a limited number of network elements. It should be appreciated that topologies illustrated in and described with reference to the accompanying FIGURES (and their teachings) are readily scalable and may accommodate a large number of components, as well as more complicated/sophisticated arrangements and configurations. Accordingly, the examples provided should not limit the scope or inhibit the broad teachings of the illustrated topologies as potentially applied to myriad other architectures.

It is also important to note that the steps in the preceding flow diagrams illustrate only some of the possible signaling scenarios and patterns that may be executed by, or within, communication systems shown in the FIGURES. Some of these steps may be deleted or removed where appropriate, or these steps may be modified or changed considerably without departing from the scope of the present disclosure. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by communication systems shown in the FIGURES in that any suitable arrangements, chronologies, configurations, and timing mechanisms may be provided without departing from the teachings of the present disclosure.

Although the present disclosure has been described in detail with reference to particular arrangements and configurations, these example configurations and arrangements may be changed significantly without departing from the scope of the present disclosure. For example, although the present disclosure has been described with reference to particular communication exchanges, embodiments described herein may be applicable to other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 142 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A method of detecting lung fluid status of a human subject, the method comprising:

performing, using a thoracic impedance measurement module coupled with a plurality of electrodes, multiple multi-wire impedance measurements on a region of interest to obtain measured impedance data, with the plurality of electrodes configured to be placed in contact with skin of a chest of the human subject, and with a number of electrodes of the plurality of electrodes used to perform the multiple multi-wire impedance measurements, the number of electrodes not exceeding eight electrodes;

comparing, by a processor coupled with the thoracic impedance measurement module, the measured impedance data to simulated impedance data obtained from a plurality of models of the region of interest;

for each model of the plurality of models, determining, by the processor, a fit of the model based on a comparison between the simulated impedance data obtained from the model and the measured impedance data; and integrating, by the processor, individual resistivity estimates obtained from the plurality of models based on a fit of the model such that an individual resistivity estimate from a better fitting model is weighted more heavily in a final resistivity estimate than another individual resistivity estimate from a worse fitting model, with the final resistivity estimate representing the lung fluid status.

2. The method of claim 1, wherein each model of the plurality of models represents a different possible combination of electrode placement and a specific anatomical feature of the human subject.

3. The method of claim 2, wherein the specific anatomical feature comprises at least one of a relative size or location of lung tissue, heart tissue, soft tissue, and bone.

4. The method of claim 1, wherein the final resistivity estimate is a weighted mean of the individual resistivity estimates.

5. The method of claim 4, wherein a weight assigned to a model N is defined by $1/f_{residual,cost,N}$, where $f_{residual,cost}$ is a residual cost function value of an optimization for solving inverse problems.

6. The method of claim 1, further comprising developing, by the processor, a single sample model using a weighted sum of the plurality of models based on a respective fit of the plurality of models.

7. The method of claim 1, wherein the multiple multi-wire impedance measurements are performed at a single excitation frequency.

8. The method of claim 1, wherein the multiple multi-wire impedance measurements are performed at multiple excitation frequencies.

9. The method of claim 8, further comprising executing, by the processor, the comparing, the determining, and the integrating for each of the multiple excitation frequencies.

10. A system, comprising:
- a plurality of electrodes configured to be placed in contact with skin of a chest of a human subject;
- a thoracic impedance measurement module coupled with the plurality of electrodes, the thoracic impedance measurement module configured to perform, using a number of electrodes of the plurality of electrodes, multiple multi-wire impedance measurements on a region of interest to obtain measured impedance data, with the number of electrodes not exceeding eight electrodes; and
- a processor coupled with the thoracic impedance measurement module and configured to,
  - compare the measured impedance data to simulated impedance data obtained from a plurality of models of the region of interest;
  - for each model of the plurality of models, determine a fit of the model based on a comparison between the simulated impedance data obtained from the model and the measured impedance data; and
  - integrate individual resistivity estimates obtained from the plurality of models based on a fit of the model such that an individual resistivity estimate from a better fitting model is weighted more heavily in a final resistivity estimate than another individual resistivity estimate from a worse fitting model,
  - with the final resistivity estimate representing lung fluid status of the human subject.

11. The system of claim 10, wherein the plurality of electrodes are connected to an elastic chest strap configured to attach around a chest of the human subject to ensure correct location of the plurality of electrodes relative to the region of interest.

12. The system of claim 10, wherein each model of the plurality of models represents a different possible combination of electrode placement and a specific anatomical feature of the human subject.

13. The system of claim 12, wherein the specific anatomical feature comprises at least one of a relative size or location of lung tissue, heart tissue, soft tissue, and bone.

14. The system of claim 10, wherein the final resistivity estimate is a weighted mean of the individual resistivity estimates.

15. The system of claim 14, wherein a weight assigned to a model Nis defined by $1/f_{residual,cost,N}$, where $f_{residual,cost}$ is a residual cost function value of an optimization for solving inverse problems.

16. The system of claim 10, wherein the thoracic impedance measurement module is further configured to develop a single sample model using a weighted sum of the plurality of models based on a respective fit of the plurality of models.

17. The system of claim 10, wherein the plurality of electrodes consists of fewer than eight electrodes.

18. The system of claim 10, wherein the plurality of electrodes has three first electrodes configured to be placed in contact with skin on the front of the chest and three second electrodes configured to be placed in contact with skin on the left side of the chest.

19. The system of claim 10, wherein the multiple multi-wire impedance measurements are performed at a single excitation frequency.

20. The system of claim 10, wherein the multiple multi-wire impedance measurements are performed at multiple excitation frequencies.

21. The system of claim 20, wherein the thoracic impedance measurement module is further configured to execute the comparing, the determining, and the integrating for each of the multiple excitation frequencies.

22. A method of detecting lung fluid status of a human subject, the method comprising:
- performing, using a thoracic impedance measurement module coupled with a plurality of electrodes, multiple multi-wire impedance measurements on a region of interest to obtain measured impedance data, with the plurality of electrodes configured to be placed in contact with skin of a chest of the human subject, and with a number of electrodes of the plurality of electrodes used to perform the multiple multi-wire impedance measurements, the number of electrodes not exceeding eight electrodes;
- summarizing, by a processor coupled with the thoracic impedance measurement module, a plurality of models of the region of interest into a single sample model that represents the region of interest;
- generating, by the processor, simulated impedance data using the single sample model;
- producing, by the processor, a final resistivity estimate for the region of interest by fitting the simulated impedance data to the measured impedance data,
- with the final resistivity estimate representing the lung fluid status.

23. The method of claim 22, further comprising, prior to the summarizing, applying, by the processor, a weight to each model of the plurality of models to produce weighted models.

24. The method of claim 23, wherein the summarizing further comprises computing a mean of a sum of weighted models.

25. The method of claim 23, further comprising fitting, by the processor, the simulated impedance data to the measured impedance data to produce weights applied to the plurality of models.

26. The method of claim 22, wherein each model of the plurality of models represents a different possible combination of electrode placement and a specific anatomical feature of the human subject.

27. The method of claim 26, wherein the specific anatomical feature comprises at least one of a relative size or location of lung tissue, heart tissue, soft tissue, and bone.

28. The method of claim 22, wherein the multiple multi-wire impedance measurements are performed at a single excitation frequency.

29. The method of claim 22, wherein the multiple multi-wire impedance measurements are performed at multiple excitation frequencies.

30. The method of claim 29, further comprising executing, by the processor, the summarizing, the generating, and the fitting for each of the multiple excitation frequencies.

31. A system, comprising:

a plurality of electrodes configured to be placed in contact with skin of a chest of a human subject;

a thoracic impedance measurement module coupled with the plurality of electrodes, the thoracic impedance measurement module configured to perform, using a number of electrodes of the plurality of electrodes, multiple multi-wire impedance measurements on a region of interest to obtain measured impedance data, with the number of electrodes not exceeding eight electrodes; and a processor coupled with the thoracic impedance measurement module and configured to, summarize a plurality of models of the region of interest into a single sample model that represents the region of interest;

generate simulated impedance data using the single sample model; and producing a final resistivity estimate for the region of interest by fitting the simulated impedance data to the measured impedance data, with the final resistivity estimate representing lung fluid status of the human subject.

32. The system of claim 31, wherein the plurality of electrodes are connected to an elastic chest strap configured to attach around a chest of the human subject to ensure correct location of the plurality of electrodes relative to the region of interest.

33. The system of claim 31, wherein each model of the plurality of models represents a different possible combination of electrode placement and a specific anatomical feature of the human subject.

34. The system of claim 33, wherein the specific anatomical feature comprises at least one of a relative size or location of lung tissue, heart tissue, soft tissue, and bone.

35. The system of claim 31, wherein the processor is further configured to develop a single sample model using a weighted sum of the plurality of models based on a respective fit of the plurality of models.

36. The system of claim 31, wherein the plurality of electrodes consists of fewer than eight electrodes.

37. The system of claim 31, wherein the plurality of electrodes has three first electrodes configured to be placed in contact with skin on the front of the chest and three second electrodes configured to be placed in contact with skin on the left side of the chest.

38. The system of claim 31, wherein the multiple multi-wire impedance measurements are performed at a single excitation frequency.

39. The system of claim 31, wherein performing the multiple multi-wire impedance measurements comprises performing the multiple multi-wire impedance measurements at multiple excitation frequencies.

40. The system of claim 39, wherein the processor is further configured to, summarize the plurality of models of the region of interest into the single sample model that represents the region of interest for each of the multiple excitation frequencies;

generate the simulated impedance data using the single sample model for each of the multiple excitation frequencies; and fit the simulated impedance data to the measured impedance data to produce a final resistivity estimate for the region of interest for each of the multiple excitation frequencies.

41. The method of claim 1, wherein the multiple multi-wire impedance measurements include multiple 4-wire impedance measurements, the method further comprising changing, by the processor, over time, a four-electrode configuration from the number of electrodes to perform different ones of the multiple 4-wire impedance measurements.

42. The method of claim 22, wherein the multiple multi-wire impedance measurements include multiple 4-wire impedance measurements, the method further comprising changing, by the processor, over time, a four-electrode configuration from the number of electrodes to perform different ones of the multiple 4-wire impedance measurements.

43. The system of claim 10, wherein the multiple multi-wire impedance measurements include multiple 4-wire impedance measurements, and wherein the processor is further configured to change, over time, a four-electrode configuration from the number of electrodes to perform different ones of the multiple 4-wire impedance measurements.

44. The system of claim 31, wherein the multiple multi-wire impedance measurements include multiple 4-wire impedance measurements, and wherein the processor is further configured to change, over time, a four-electrode configuration from the number of electrodes to perform different ones of the multiple 4-wire impedance measurements.

* * * * *